United States Patent [19]

Greenblatt et al.

[11] Patent Number: 4,843,318
[45] Date of Patent: Jun. 27, 1989

[54] DISTANCE COMPENSATION IN MAGNETIC PROBE TESTING SYSTEMS WHEREIN OBJECT TO PROBE SPACING IS EMPLOYED AS AN EXPONENT IN EXCITINGS PROBES OR PROCESSING PROBE OUTPUTS

[75] Inventors: Stanley Greenblatt, Bronx; Richard H. Colman, New Rochelle; Edward D. Spierer, Belle Harbor, all of N.Y.

[73] Assignee: Magnetic Analysis Corporation, Mount Vernon, N.Y.

[21] Appl. No.: 73,703

[22] Filed: Jul. 15, 1987

[51] Int. Cl.$^4$ .................... G01N 27/72; G01N 27/82; G01R 33/00
[52] U.S. Cl. .................................. 324/225; 324/227; 324/238
[58] Field of Search ......... 324/225, 227, 232, 234–242

[56] References Cited

U.S. PATENT DOCUMENTS 4,528,506   7/1985   Davis et al. ......................... 324/225

Primary Examiner—Reinhard J. Eisenzopf
Assistant Examiner—Walter E. Snow
Attorney, Agent, or Firm—Robin, Blecker & Daley

[57] ABSTRACT

A system is disclosed for nondestructive object testing comprising a magnetic probe responsive to an excitation signal for generating a magnetic field and thereby inducing eddy-currents in the object. The probe further provides an output signal indicative of the presence of a flaw in the object. A distance sensor generates an output signal indicative of the spacing of the probe from the object. Circuitry is provided for receiving the distance sensor output signal and is responsive thereto to supply such excitation signal to the probe. The circuitry employs the distance indication in the distance sensor output signal as an exponent in generating the excitation signal.

19 Claims, 5 Drawing Sheets

DISTANCE COMPENSATION IN MAGNETIC PROBE TESTING SYSTEMS WHEREIN OBJECT TO PROBE SPACING IS EMPLOYED AS AN EXPONENT IN EXCITINGS PROBES OR PROCESSING PROBE OUTPUTS

FIELD OF THE INVENTION

This invention relates generally to nondestructive testing sytems and pertains more particularly to systems of the type having magnetic probes disposed in sensing relation to test objects and adapted to provide output signals indicative of flaws therein.

BACKGROUND OF THE INVENTION

Two types of magnetic nondestructive systems are in widespread use currently, namely, the "eddy-current" system and the "flux leakage" system. In the former system, probes adjacent a test object are excited and apply a magnetic field thereto which induces eddy-currents in the object. In the latter system, probes adjacent the test object measure flux leakage therefrom. In both systems, the probe output signals vary in characteristics when a flaw in the specimen is encountered and associated analyzing circuitry receives the probe output signals and provides system output indication of object faults.

Both of the described systems are susceptible to variation in probe output signal magnitude as spacing between the probe and the specimen varies. For a given probe and flaw, applicants herein have observed that the ratio of probe output signal amplitudes over a range of one hundred and fifty mils may vary by as much as a factor of fifty. Thus, a flaw measurement signal at the closest location to the object in such range may have an amplitude of fifty times that of the measurement signal at a location spaced one hundred and fifty mils from such closest location. Evidently, in the absence of some compensation for this signal strength variation, flaws present in an object can go undetected at probe spacings distal therefrom.

Constancy of probe spacing in relation to the object is fully implausible as a solution to the problem. Thus, an object may exhibit surface depth irregularity in substantial measure, whereby a fixedly positioned probe would experience a large spacing range. Further, it is typical that measurements are made with relative motion as between the object and the probes in which case spacing variation occurs even where a specimen might itself have surface depth variation of quite low magnitude.

Known efforts to solve this problem are considered to be empirical or at least not as analytical as would be desirable to fully address a solution. Typically, the prior art has addressed the problem with an outset recognition that the probe output signal must somehow be attenuated greatly at close location in the spacing range, with attenuation then being successively less as the outside location of the spacing range is reached. One practice in this respect is seen in U.S. Pat. No. 3,611,120, wherein the probe includes an L-C circuit which is designed to exhibit resonance at the outside location of the spacing range and to be loaded inductively by the object as the probe approaches the specimen. Gain through the probe is thus lessened as the departure from resonance increases by probe loading by the object.

Perhaps a better understanding of the reach of this type of compensation is seen from commercially-available eddy-current type distance sensors of the Electro Corporation, one of which is discussed below for use in the subject invention. Such device is of the resonance at maximum spacing variety, employing variation in the "Q" of the device to provide output indication of spacing. Literature discussion of this device indicates that quite close linearity is obtainable and is precisely indicative of probe spacing as induced eddy-currents sap field energy in a linear manner.

Attainment of linearity of attenuation with distance is seen by applicants to be an incomplete solution to the problem at hand, since they note, as is fully developed below, that spacing or distance is but one input to the solution of such problem.

SUMMARY OF THE INVENTION

A primary object of the present invention is to provide systems and methods for enchancing the accuracy of compensation for probe-to-object spacing variation in the course of magnetic object examination.

In attaining this and other objects, applications look at the outset to the identification of a mathematical relation which attends the output signals of a given probe structure with distance from an object over a spacing range. Such relation is found to be inversely exponential with increasing distance, from the object in such range, the exponent being the product of distance and a constant determinable for different probe structures.

Upon such determinations, applicants compensate system performance by the use of circuitry which fully complements the above mathematical relation, such that the input provided to the system flaw analysis circuitry is constant for a given observed defect in the object, irrespective of the location of the probe in the spacing range.

In a preferred embodiment for the eddy-current type of system, discussed in detail below, the system of the invention includes a drive source providing a cyclic excitation voltage typically directly serving the probes in prior art systems, but otherwise functioning herein as an input for a drive variator circuit. The probe includes a distance transducer, which may be of the above-noted commercially-available type, providing an output signal at all times indicative of the spacing between the probe and the specimen. The output signal of the distance transducer is connected as one control input to the drive variator circuit. The output of the drive variator circuit is furnished to the probe as excitation for the probe eddy-current coil.

In this embodiment, the drive variator circuit is configured to complement the inverse exponential relation, determined to underlie the system probe and object spacing variation, by providing a direct exponential multiplier therefor. The aforesaid distance tranducer output signal provides one factor of such exponent and the drive variator is further configured to accept a second factor of such exponent, which is related to the composition of the probe housing.

The foregoing and other object and features of the invention will be further understood from the following detailed description of preferred embodiments of the invention and from the drawings wherein like reference numerals identify like parts and components throughout.

DETAILED DESCRIPTION OF PEFERRED EMBODIMENTS AND PRACTICES

Figure 1:
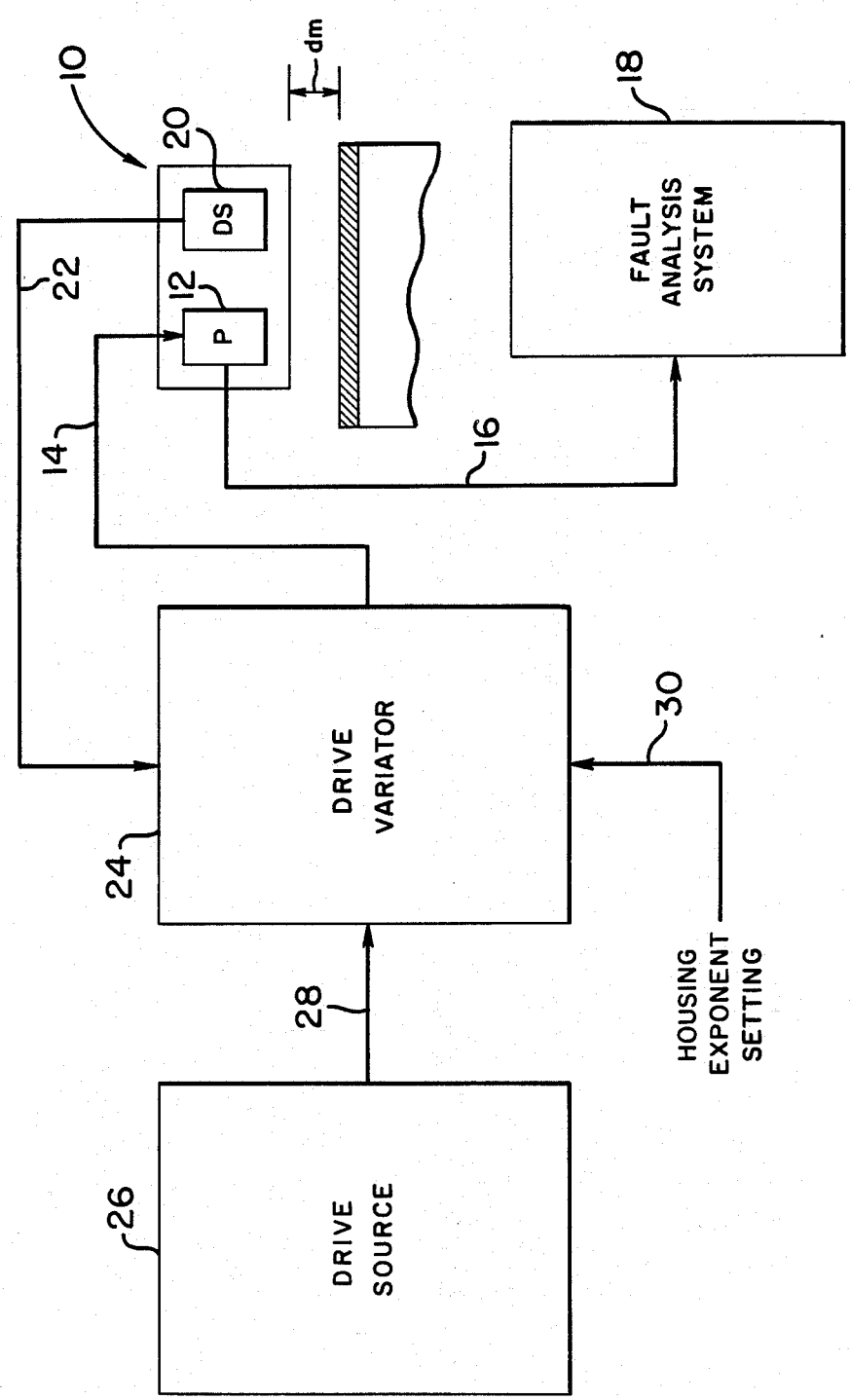
FIG. 1 is a functional block diagram of the preferred embodiment of an eddy-current system in accordance with the invention, also showing a test object in part and in section.

Referring to FIG. 1, the eddy-current system therein depicted includes probe housing 10, which encases probe (P) 12 excited over line 14 and providing output signals over line 16 to fault analysis circuitry 18. Circuitry 18 is not further discussed, since it may take various forms well known in the art, for example, in-phase and quadrature channels providing a polar display on an oscilloscope.

Commonly disposed with probe 12 in probe housing 10 is a distance sensor (DS) 20 which furnishes its output signals over line 22 to drive variator 24. Sensor 20 may be comprised of a displacement transducer commercially obtainable under the trademark EMDT from Electro Corporation, PA12D AND PAD12 series. As described in Electro literature, this type of transducer employs a very low level radio frequency field to generate eddy-currents in any metal target which the field intercepts. Such eddy-currents remove energy from the field, reducing the apparent Q (qualify factor) of the sensor and providing output signals indicative of the distance between the sensor and the target.

A test object in the form of a metal pipe is shown adjacent probe housing 10 in FIG. 1 and the literals, dm (distance maximum), are intended to indicate the maximum spacing in the prescribed range of spacing between the probe housing and the pipe.

Drive source 26 is of customary nature, providing an output signal of cyclic, typically sinusoidal or square wave, variety normally applied directly to a probe in an eddy-current system for excitation thereof. In accordance with the present invention, such signal is provided over the line 28 to drive variator 24. A further input to drive variator 24 shown in FIG. 1 is provided on line 30 (housing exponent setting) for purposes discussed below after consideration of the FIG. 2 detailed block diagram of drive variator 24.

Figure 2:
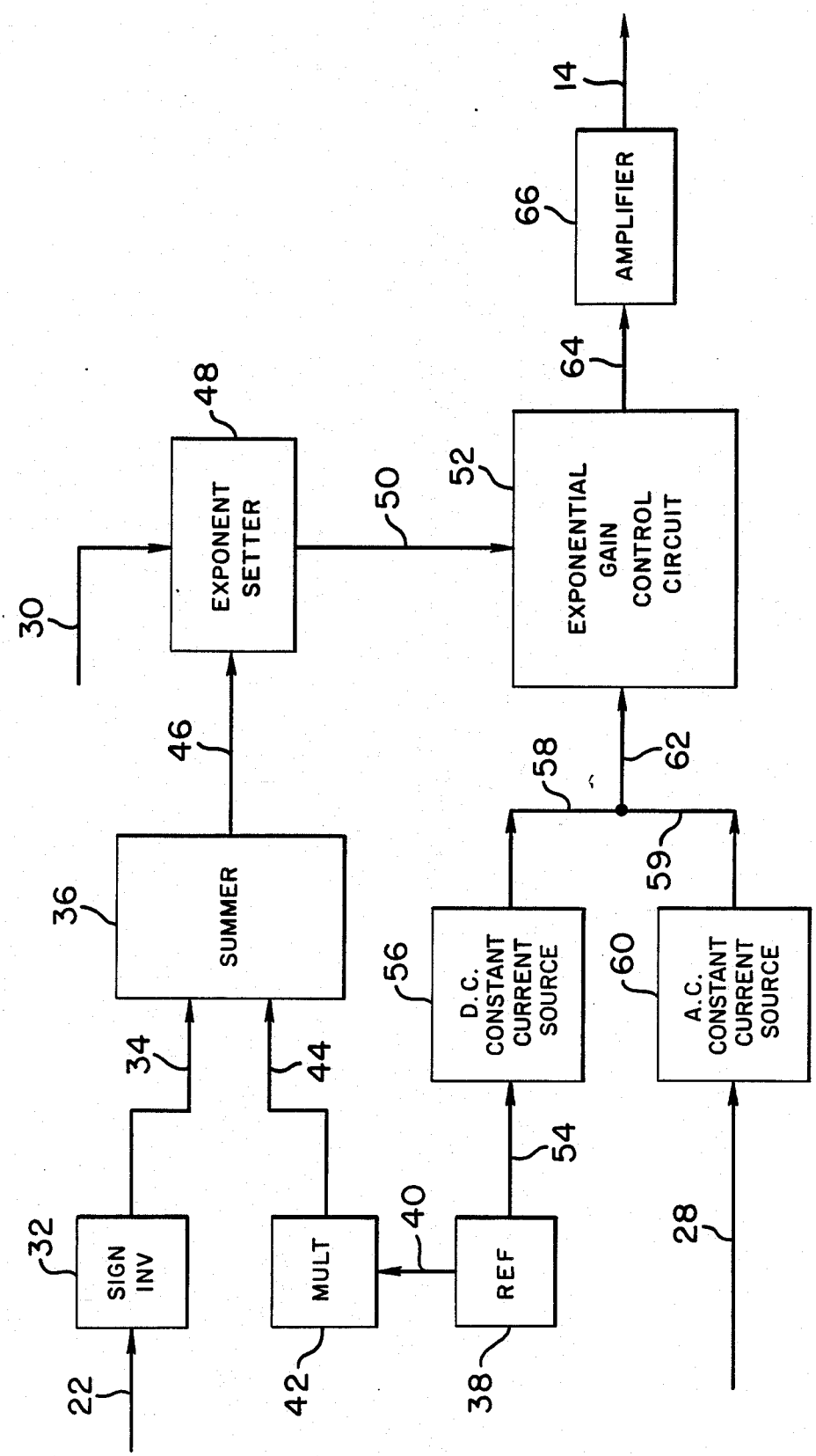
FIG. 2 is detailed block diagram of components of the drive variator the FIG. 1 system.

Turning to FIG. 2, the three inputs to drive variator 24 are carried over from FIG. 1 and include line 22 (distance sensor 20 output), line 28 (cyclic drive input) and line 30 (housing exponent setting). Output line 14 of FIG. 1 is likewise carried over to FIG. 2. Describing the FIG. 2 components, line 22 feeds signs inverter (SIGN INV) 32, the output of which is applied over line 34 to summer circuit 36. A five-volt reference source (REF) 38 applies its output over line 40 to mutiplier 42 which provides a second input to summer circuit 36 over line 44. The summer circuit 36 output is applied over line 46 to housing exponent setter 48. The latter is responsive to the input on line 30 to provide its output signal on line 50 to exponential gain control circuit 52.

The output of reference source 38 is also applied over line 54 to d.c. constant current source 56 which furnishes its output over line 58. Line 28 applies the cyclic drive input signal to a.c. constant current source 60 which applies its output to line 59 for summing with the line 58 signal, the composite being applied to line 62 and thence to exponential gain control circuit 52. The output of circuit 52 is furnished over line 64 to amplifier 66 which in turn feeds output line 14.

By exciting probe 12 of FIG. 1 directly from drive source 26 of FIG. 1, applicants find that the flaw amplitude, as seen in the probe output signal, may be expressed as follows:

$$FA = K_S e^{-ax} \quad (1),$$

where FA is flaw amplitude, $K_S$ is a constant, x is the spacing of the probe from the specimen, and a is a further constant related to the probe housing material.

The premise of applicant's eddy-current probe spacing compensation is to output an $e^{ax}$ signal and to drive the probe with such signal. By this practice, applicants drive the probe with the complement of its inherent output signal and attain a unity relationship as between field and probe output at all distances within the spacing range of interest. The manner in which this is accomplished in FIG. 2 will now be explained.

The output ($DS_{out}$) of distance sensor 20 of FIG. 1, provided on line 22 as an input to FIG. 2 may be expressed as follows in d.c. volts:

$$DS_{out} = 10x/dm \quad (2),$$

where dm is the aforesaid maximum spacing. As is seen, scaling is such that when x is equal to dm, the output of distance sensor 20 is ten d.c. volts.

The output of sign inverter 32 is $-10x/dm$. The signal on line 44 is $+10$ d.c. volts, reached by multiplication by two in multiplier 42 of the five d.c. volt output of reference circuit 38.

The output ($SUM_{out}$) of summer circuit 36 may be expressed as follows:

$$SUM_{out} = (10 - (10x/dm)) \quad (3).$$

Exponent setter circuit 48 variably scales its input and provides the output: $((a)dm/10)(10-(10x/dm)))$, where a is the probe housing exponent factor above discussed. This composite signal on line 50 serves to set an exponent accordingly in the circuit 52 output.

The line 62 input signal ($I_{in}$) to circuit 52 may be expressed as follow:

$$I_{in} = I_{d.c.} + I_{a.c.} \quad (4),$$

where $I_{d.c.}$ is furnished by d.c. constant current source 56 and serves to bias circuit 52, and $I_{a.c.}$ is furnished by a.c. constant current source 60 in response to the customary probe excitation signal on line 28.

Circuit 52, also known in the art as an antilog circuit, functions to output (Cir $52_{out}$) as follows:

$$\text{Cir } 52_{out} = (I_{in})(K_{Cir\ 52})\ (e-\text{exponent input}) \quad (5).$$

For the example under discussion, the first two factors are constant or repetitive with time. The last factor becomes the following:

$$e^{-(((a)dm/10)(10-(10x/dm)))} \quad (6).$$

which may be reduced to:

$$e^{-(a)dm}e^{(a)x} \quad (7).$$

Since, however, $e^{-(a)dm}$ is a constant, the output of circuit 52, in its variable makeup, is proportional to $e^{ax}$. The output of circuit 52 now meets the stated premise of the system and practice of the invention, namely, wherein, setting aside constants, line 64 provides a drive signal for probe 12 which will drive the probe, by amplication in amplifier 66, at the complement ($e^{ax}$) of the probe and object spacing relationship ($e^{-ax}$). Drive and response for the probe are thus distance insensitive and spacing, through variable, is fully compensated.

Figure 3A:
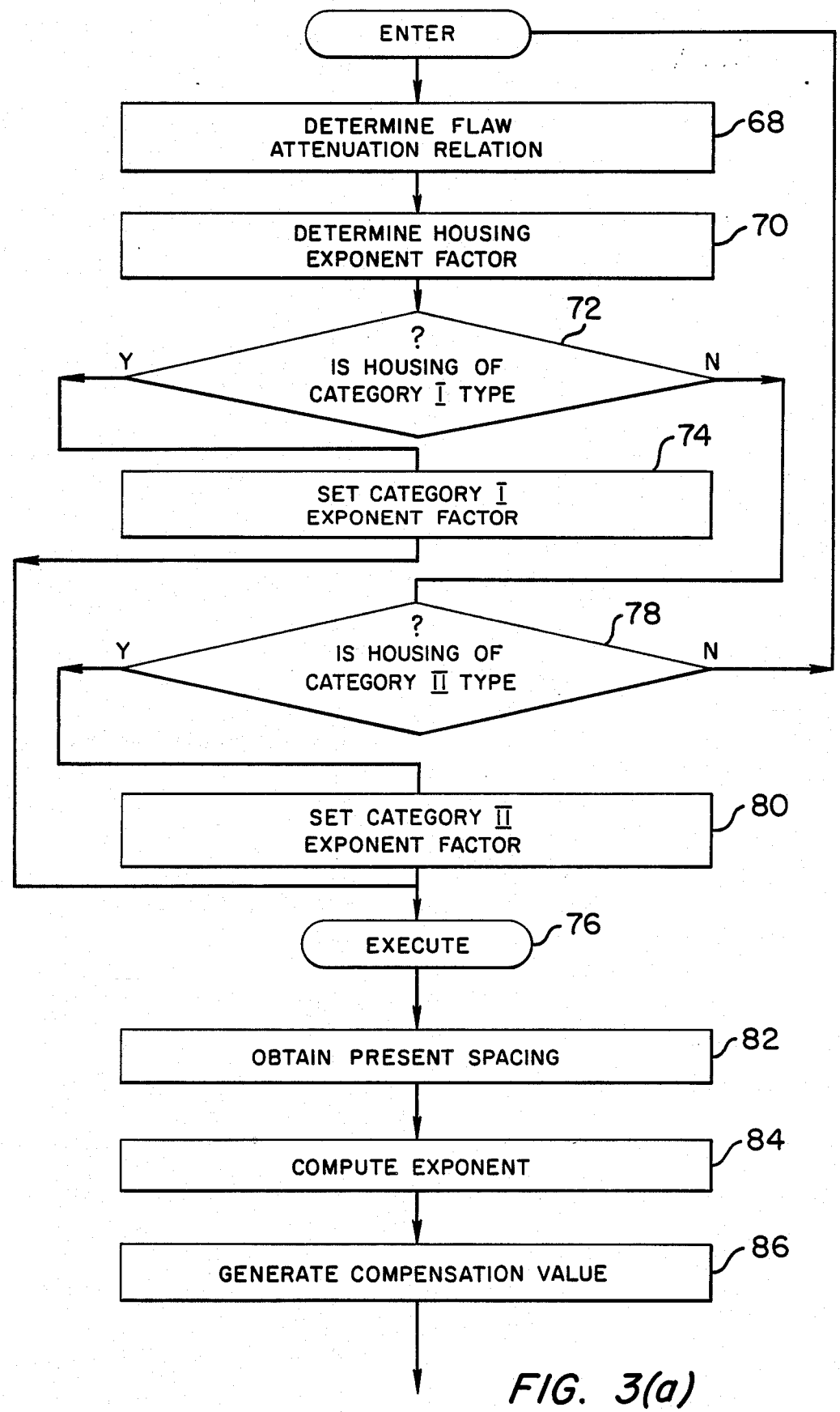
FIGS. 3(a) and 3(b) are a flow chart of practice in accordance with the invention and adapted to both eddy-current systems and flux-leakage systems.
Figure 3B:
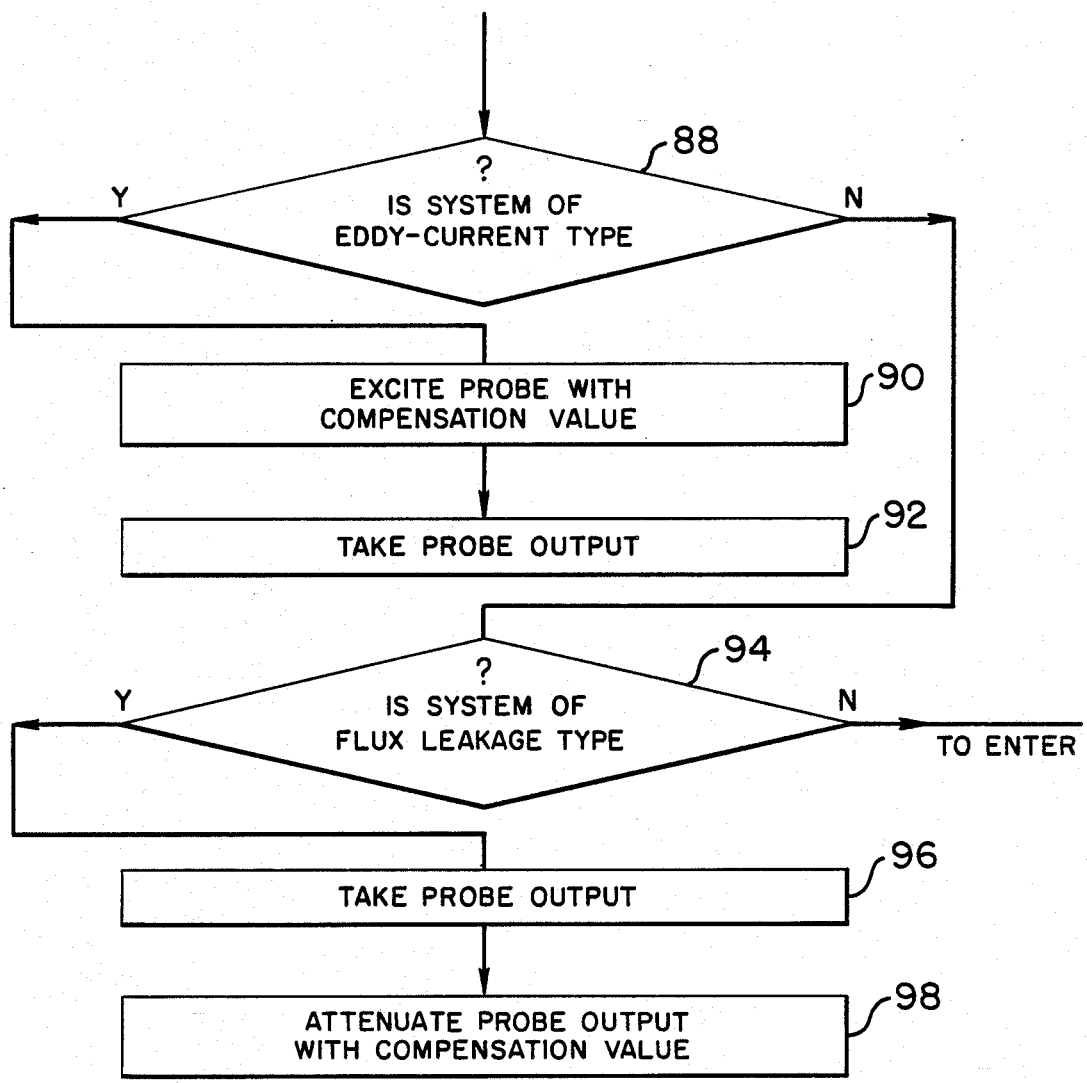

Turning to FIGS. 3(a) and 3(b), the flow chart thereof both summarizes practice in accordance with the invention and provides insight into application thereof to a flux leakage type system as well as the eddy-current type system.

Following ENTER, step 68 of FIG. 3(a) (DETERMINE FLAW ATTENUATION RELATION) calls for a determination of a physical oR mathematical relationship definitive of fault attenuation, as would be seen by a probe, in variable spacing relation to a specimen, under the influence of a magnetic field of cyclic character, whether generated by a probe (eddy-current system) or by pole pieces independently of the probe (flux leakage).

Per applicants' finding, such relationship may be probe housing dependent in part, where different probes are available for use. Step 70 (DETERMINE HOUSING EXPONENT FACTOR) calls for the determination of the applicable housing contribution to the generic relationship obtaing from step 68 practice. Here, initial inquiry is made in step 72 (? IS HOUSING OF CATEFORY I TYPE) as to whether the probe housing falls into category I, which may be inquiry as to whether the probe housing is ferromagnetic. If the response to this inquiry is positive, practice proceeds to step 74 (SET CATEGORY I FACTOR), wherein the exponent scaling factor is set to that for ferromagnetic housing material and practice proceeds directly to step 76 (EXECUTE). if negative response is made to the inquiry of step 72, practice proceeds to step 78 (? IS HOUSING OF CATEGORY II TYPE), wherein inquiry is made as to whether the probe housing falls into category II, different from that of category I, e.g., as to whether the housing aluminum. If the response is positive, the flow steps to step 80 (SET CATEGORY II FACTOR), wherein the exponent scaling factor is set to that for aluminum, and practice proceeds to step 76 for execution. It will understood that various other housing categories may be involved, and the described practice will step through all such categories. On the other hand, if but a single probe housing is available, practice would step from step 70 to step 76.

In the execute phase, step 82 (OBTAIN PRESENT SPACING) is first practiced, whereby the output of the distance sensor is taken. In step 84 (COMPUTE EXPONENT), the aforementioned ax or x will be determined. The compensation value or signal is then provided in step 86 (GENERATE COMPENSATION VALUE).

Carrying over to FIG. 3(b), inquiry is made in step 88 (? IS SYSTEM OF EDDY-CURRENT TYPE) as to whether practice involves probe spacing compensation in an eddy-current system involved in the current testing. If the inquiry is answered in the affirmative, practice proceeds to step 90 (EXCITE PROBE WITH COMPENSATION VALUE), thus calling for the aforementioned probe excitation with the complement of the predetermined relationship from step 68. In this mode, step 92 (TAKE PROBE OUTPUT) provides for direct usage of the probe output signal in the system analyzing circuitry.

Upon negative response to the step 88 inquiry, practice proceeds to step 94 (? IS SYSTEM OF FLUX LEAKAGE TYPE) wherein question is raised as to whether the system involved in the current testing is of the flux leakage type. If the question is answered in the affirmative, step 96 (TAKE PROBE OUTPUT) calls for reading the probe output signal. However, since excitation in this system is by pole piece field generation and is accordingly not changeable at sampling rates of interest, the probe output is not used directly by system analyzing circuitry but is first modified in compensating manner, e.g., per the $e^{ax}$ correction, in step 98 (ATTENUATE PROBE OUTPUT WITH COMPENSATION VALUE).

Turning now to the specific circuit embodiment for exponential gain control circuit 52, the operational amplifier and resistor arrangement A1, R1 and R2 serves to produce a constant d.c. current, and corresponds with circuit elements 38, 54 and 56 of FIG. 2. The operational amplifier and resistor arrangement A2, R3 and R4 serves to change the sign of the distance indication signal on line 22 and to sum same with the multiplied by two five volt level applied to the upper input of A2. This curcuitry combines and implements the functions of circuit elements 32 through 44 of FIG. 2.

The operational amplifier and resistor arrangement A3 and R8–R11 is an a.c. constant current source, capacitor C1 serving to block any d.c. input to A3, and is counterpart to circuit element 60 of FIG. 2.

Figure 4:
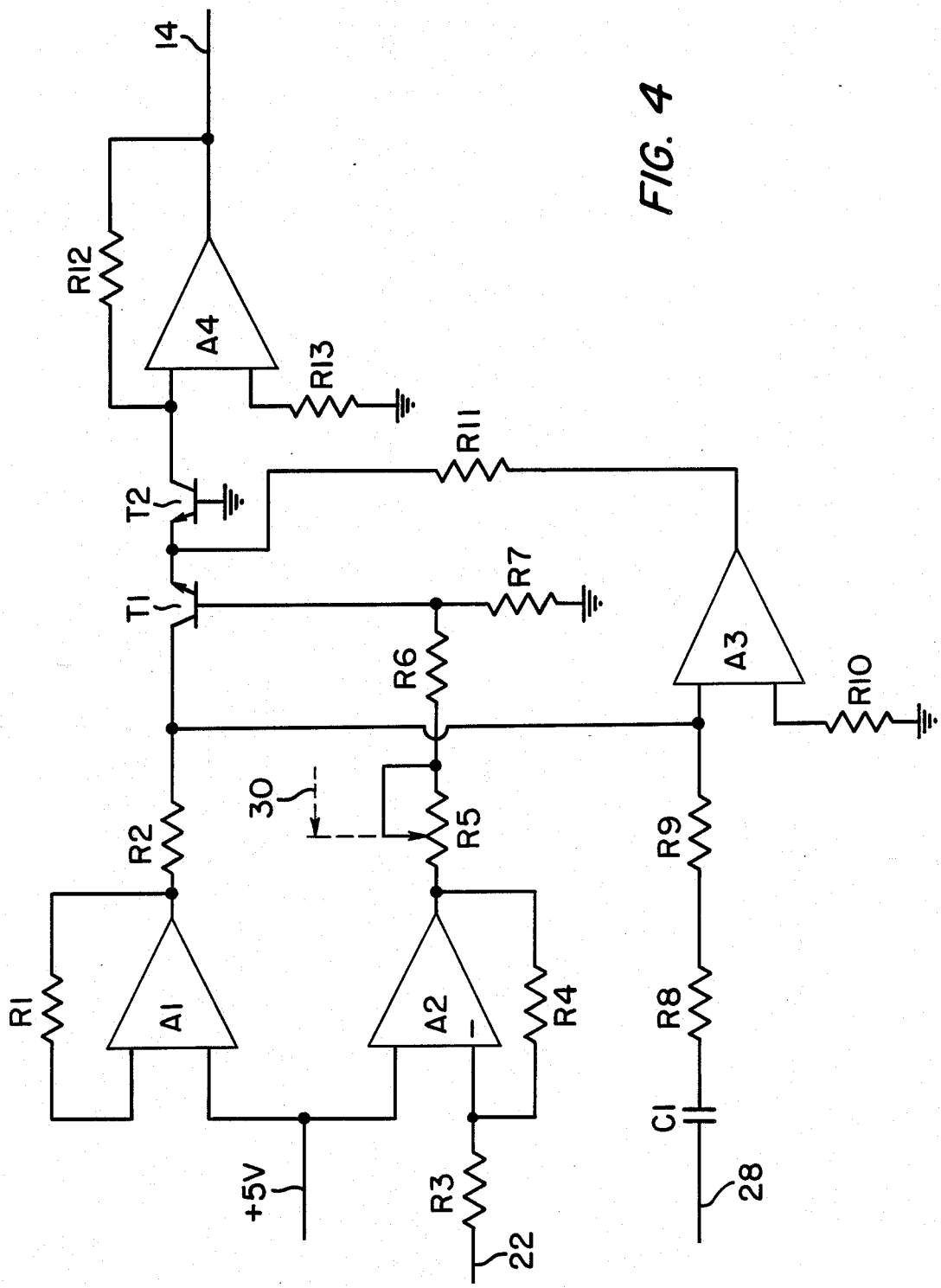
FIG. 4 is an electrical schematic drawing of a preferred circuit embodiment of the drive variator of FIG. 1 wherein certain components of the FIG. 2 block diagram are merged into common circuitry.

Transistor T1 functions as the exponential signal generator for probe excitation and may be regarded as having a first input terminal connected to its base and coupled through R5–R7 to the operational amplifier and resistor arrangement providing the spacing control information. T1 may likewise be seen as having a second input terminal connected to its collector and receiving the sum of the d.c. and a.c. constant currents from R2 and R9. R5 is variable settable by input 30 to its wiper in accordance with the applicable housing category. Transistor T1 may also be seen as having an output terminal, its emitter, which furnishes a current according with the desired compensating relation through transistor T2 into R12 of the operational amplifier and resistor arrangement A4, R12 and R13. Transistor T2 and resistor R7 are temperature-compensating in nature. Amplifier 66 of FIG. 2 may be realized by parallel drivers (not shown in FIG. 4) interposed between A4 and line 14.

By way of summary of the foregoing and introduction to the ensuing claims, it will be seen that the invention provides a system for nondestructive object testing comprising a magnetic probe responsive to an excitation signal for generating a magnetic field and thereby inducing eddy-currents in the object. The probe further provides an output signal indicative of the presence of a flaw in the object. A distance sensor generates an output signal indicative of the spacing of the probe from the object. Circuitry is provided for for receiving the distance sensor means output signal and is responsive thereto to supply such excitation signal to the probe.

The circuitry employs the distance indication in the sensor output signal as an exponent in generating the excitation signal.

In its functional makeup, such circuitry includes a first circuit for subtracting the distance sensor output signal from a constant signal and provides a signal indicative of such difference, a constant current source providing d.c. and and a.c. currents, and an exponential circuit having a first input terminal receiving such difference signal and a second input terminal receiving the currents provided by the constant current source and an output terminal furnishing the excitation signal.

In the specific probe and object spacing relation addressed above, such circuitry furnishes the excitation signal at least in part in accordance with the relation $e^x$, where x is the spacing indication in the distance sensor output signal.

Where probe characteristics vary among available probes, the circuitry furnishes the excitation signal at least in part in accordance with the relation $e^{ax}$, where a is indicative of a probe characteristic.

In a method aspect, the invention addresses a method for nondestructive detection of flaws in an object by the use of a magnetic field and a magnetic probe in variable spacing relation to such object, and will be seen to introduce the following steps. One predetermines an exponential relationship for flaw indication by the probe with respect to spacing thereof from an object using a cyclic magnetic field. One senses the spacing between said probe and an object under evaluation and employs such sensed spacing to generate a signal indicative of an exponential relationship complementary to such predetermined exponential relationship. Such generated signal may be used, in eddy-current systems, for controlling the magnetic field used in such testing of said object. In flux leakage system application, the generated signal is used in processing output signals of said probe, as by attenuating same.

Various changes to the foregoing systems and components and modifications to the described practices may be introduced without departing from the invention. Accordingly, it is to be understood that the particularly discussed and depicted preferred embodiments and methods are intended in an illustrative and not in a limiting sense. The true spirit and scope of the invention is set forth in the following claims.

What is claimed is:

1. A system for nondestructive object testing comprising:
    (a) magnetic probe means responsive to an excitation signal for generating a magnetic field and thereby inducing eddy-currents in said object, said probe means further providing an output signal indicative of the presence of a flaw in said object;
    (b) distance sensing means for generating an output signal indicative of the spacing of said probe means from said object; and
    (c) circuit means for receiving said distance sensing means output signal and responsive thereto to supply said excitation signal to said probe means, said circuit means employing the spacing indication in said sensing means output signal as an exponent in generating said excitation signal for controlling the amplitude of said excitation signal.

2. The invention claimed in claim 1 wherein said probe means is encased in a probe housing, said system including means for generating a signal indicative of a characteristic of said probe housing, and wherein said circuit means is further responsive to said signal indicative of a characteristic of said probe housing, said circuit means also employing such characteristic indication as an exponent in generating said excitation signal for controlling the amplitude of said excitation signal.

3. The invention claimed in claim 1 further including a drive source providing a cyclic output signal and wherein said circuit means receives said drive source output signal and employs same as a component of a signal multiplied exponentially by the spacing indication in said distance sensing means output signal in the generation of said excitation signal.

4. The invention claimed in claim 1 wherein said circuit means comprises:
    (a) first circuit means for subtracting said distance sensing means output signal from a constant signal and providing signal indicative of said difference;
    (b) constant current source means for providing d.c. and an a.c. currents; and
    (c) an exponential circuit having a first input terminal receiving such difference signal and a second input terminal receiving the currents provided by said constant current source and an output terminal furnishing said excitation signal.

5. The invention claimed in claim 4 wherein said exponential circuit includes a transistor having its base in series circuit with said first input terminal and its collector in series circuit with said second terminal.

6. The invention claimed in claim 2 wherein said circuit means comprises:
    (a) first circuit means for subtracting said distance sensing means output signal from a constant signal and providing signal indicative of such difference;
    (b) second circuit means for receiving such difference signal and said characteristic indication and providing an output signal indicative of said difference signal modified by said characteristic indication;
    (c) constant current source means for providing d.c. and an a.c. currents; and
    (d) an exponential circuit having a first input terminal receiving said second circuit means output signal and a second input terminal receiving the currents provided by said constant current source and an output terminal furnishing said excitation signal.

7. The invention claimed in claim 6 wherein said exponential circuit includes a transistor having its base in series circuit with said first input terminal and its collector in series circuit with said second terminal.

8. A system for nondestructive object testing comprising:
    (a) magnetic probe means responsive to an excitation signal for generating a magnetic field and thereby inducing eddy-currents in said object, said probe means further providing an output signal indicative of the presence of a flaw in said object;
    (b) distance sensing means for generating an output signal indicative of the spacing of said probe means for said object; and
    (c) circuit means for receiving said distance sensing means output signal and furnishing said excitation signal at least in part in accordance with the relation $e^x$, where x is the spacing indication in said distance sensing means output signal.

9. The invention claimed in claim 8 wherein said probe means is encased in a probe housing, said system including means for generating a signal indicative of a characteristic of said probe housing, and wherein said circuit means is further responsive to said signal indicative of a characteristic of said probe housing, said circuit means furnishing said excitation signal at least in part in accordance with the relation $e^{ax}$, where a is such characteristic indication.

10. The invention claimed in claim 8 wherein said circuit means comprises:
    (a) first circuit means for subtracting said distance sensing means output signal from a constant signal and providing signal indicative of such difference;
    (b) constant current source means for providing d.c. and an a.c. currents; and
    (c) an exponential circuit having a first input terminal receiving such difference signal and a second input terminal receiving the currents provided by said constant current source and an output terminal furnishing said excitation signal.

11. The invention claimed in claim 10 wherein said exponential circuit includes a transistor having its base in series circuit with said first input terminal and its collector in series circuit with said second terminal.

12. The invention claimed in claim 9 wherein said circuit means comprises:
    (a) first circuit means for subtracting said distance sensing means output signal from a constant signal and providing signal indicative of such difference;
    (b) second circuit means for receiving such difference signal and said characteristic indication and providing an output signal indicative of said difference signal modified by said characteristic indication;
    (c) constant current source means for providing d.c. and an a.c. currents; and
    (d) an exponential circuit having a first input terminal receiving said second circuit means output signal and a second input terminal receiving the currents provided by said constant current source and an output terminal furnishing said excitation signal.

13. The invention claimed in claim 12 wherein said exponential circuit includes a transistor having its base in series circuit with said first input terminal and its collector in series circuit with said second terminal.

14. In a method for nondestructive detection of flaws in an object by the use of a magnetic field and a magnetic probe in variable spacing relative to such object, the steps of:
    (a) predetermining an exponential relationship for flaw indication by said probe with respect to spacing thereof from an object using a cyclic magnetic field;
    (b) sensing the spacing between said probe and an object under evaluation; and
    (c) employing such sensed spacing as an exponent in generating a signal indicative of an exponential relationship complementary to such predetermined exponential relationship.

15. The invention claimed in claim 14 wherein such generated signal is employed for controlling the magnetic field used in such testing of said object.

16. The invention claimed in claim 15 wherein said probe is an eddy-current probe and wherein said probe produces said magnetic field to induce eddy-currents in said object in acordance with such generated signal.

17. The invention claimed in claim 16 wherein said probe exhibits one of several characteristics in accordance with the composition thereof, including the further step of employing the applicable characteristic of said probe in obtaining said predetermined exponential relationship and in generating said signal indicative of said exponential relationship complementary to said predetermined exponential relationship.

18. The invention claimed in claim 14 wherein such generated signal is employed in processing output signals of said probe.

19. The invention claimed in claim 18 wherein said probe exhibits one of several characteristics in accordance with the composition thereof, including the further step of employing the applicable characteristic of said probe in obtaining said predetermined exponential relationship and in generating said signal indicative of said exponential relationship complementary to said predetermined exponential relationship.

* * * * *